US011221325B2

(12) United States Patent
Okamoto et al.

(10) Patent No.: US 11,221,325 B2
(45) Date of Patent: *Jan. 11, 2022

(54) DEVICE FOR CONCENTRATION AND SEPARATION OF CIRCULATING TUMOR CELLS, AND METHOD FOR CONCENTRATION AND SEPARATION OF CIRCULATING TUMOR CELLS

(71) Applicant: SEKISUI MEDICAL CO., LTD., Tokyo (JP)

(72) Inventors: Ryusuke Okamoto, Shunan (JP); Tomonori Inoue, Shunan (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 665 days.

This patent is subject to a terminal disclaimer.

(21) Appl. No.: 15/025,458

(22) PCT Filed: Sep. 30, 2014

(86) PCT No.: PCT/JP2014/076004
§ 371 (c)(1),
(2) Date: Mar. 28, 2016

(87) PCT Pub. No.: WO2015/046557
PCT Pub. Date: Apr. 2, 2015

(65) Prior Publication Data
US 2016/0223521 A1    Aug. 4, 2016

(30) Foreign Application Priority Data

Sep. 30, 2013 (JP) .............................. JP2013-203613

(51) Int. Cl.
*G01N 33/50* (2006.01)
*G01N 1/40* (2006.01)
*G01N 33/49* (2006.01)
*G01N 33/574* (2006.01)

(52) U.S. Cl.
CPC ....... *G01N 33/5002* (2013.01); *G01N 1/4077* (2013.01); *G01N 33/491* (2013.01); *G01N 33/574* (2013.01); *G01N 2001/4083* (2013.01); *G01N 2333/70596* (2013.01)

(58) Field of Classification Search
CPC ............. G01N 33/5002; G01N 33/491; G01N 1/4077; G01N 33/574; G01N 2001/4083; G01N 2333/70596
See application file for complete search history.

(56) References Cited

U.S. PATENT DOCUMENTS

| 4,021,340 A | 5/1977 | Zine, Jr. |
| 4,190,535 A | 2/1980 | Luderer et al. |
| 6,448,075 B1 | 9/2002 | Thomas et al. |
| 8,623,655 B2 * | 1/2014 | Anraku ................. G01N 33/491 137/544 |
| 8,642,343 B2 * | 2/2014 | Inoue .................... G01N 33/491 422/430 |
| 8,795,957 B2 * | 8/2014 | Inoue ..................... A61B 5/154 435/2 |
| 2002/0009440 A1 | 1/2002 | Thomas et al. |
| 2003/0092078 A1 | 5/2003 | Thomas et al. |
| 2003/0185817 A1 * | 10/2003 | Thomas ................. C07K 16/28 424/140.1 |
| 2004/0197904 A1 | 10/2004 | Thomas et al. |
| 2010/0195413 A1 | 8/2010 | Shimizu et al. |
| 2012/0070350 A1 * | 3/2012 | Anraku ................... C08L 71/02 422/547 |
| 2012/0308446 A1 * | 12/2012 | Inoue ................... G01N 33/491 422/547 |
| 2015/0056649 A1 | 2/2015 | Araki et al. |

FOREIGN PATENT DOCUMENTS

| CN | 1367876 A | 9/2002 |
| CN | 101587043 A | 11/2009 |
| CN | 102741690 A | 10/2012 |
| CN | 102770762 A | 11/2012 |
| JP | 54-126718 A | 10/1979 |
| JP | 10-10121 A | 1/1998 |
| JP | 1010121 A * | 1/1998 |
| JP | 2012-21828 A | 2/2012 |
| JP | 2012-22002 A | 2/2012 |
| JP | 2013-42689 A | 3/2013 |
| WO | WO-2011/105253 A1 | 9/2011 |
| WO | WO-2011105253 A1 * | 9/2011 |
| WO | WO-2012/154257 A1 | 11/2012 |
| WO | WO-2013/105612 A1 | 7/2013 |

OTHER PUBLICATIONS

The First Office Action for the Application No. 2014800539617 from The State Intellectual Property Office of the People's Republic of China dated Apr. 6, 2017.
Notification of Reasons for Refusal for the Application No. 2015-539449 from Japan Patent Office dated May 23, 2017.
"Instructions 71-7167-00 AG Ficoll-Paque PLUS", GE Healthcare Bio-Sciences AB, 2007.
Written Opinion of the International Searching Authority (PCT/ISA/237) for Application No. PCT/JP2014/076004 dated Dec. 2, 2014 (English Translation mailed Apr. 14, 2016.
Yamada, Shito et al., "Studies on the Cytologic Diagnosis of the Stomach-Cancer". The Journal of the Japanese Society of Internal Medicine, 1960, vol. 49, No. 2, pp. 142-147.

(Continued)

*Primary Examiner* — Tracy Vivlemore
*Assistant Examiner* — Nam P Nguyen
(74) *Attorney, Agent, or Firm* — Cheng Law Group, PLLC

(57) ABSTRACT

To provide a device for concentration and separation of circulating tumor cells, capable of recovering circulating tumor cells in a blood-derived specimen simply, at a high recovery rate, and with low invasion of the tumor cells. A device for concentration and separation of circulating tumor cells present in a blood-derived specimen, in which a cell separating agent with thixotropic property having a specific gravity ranging from 1.050 to 1.080 and enabling the separation of tumor cells and blood cells other than the tumor cells by a centrifugal operation is housed in a bottomed tube-shaped container closed at one end and opened at the other end.

14 Claims, 1 Drawing Sheet

(56) References Cited

OTHER PUBLICATIONS

Gerges, Noha et al., "New technologies for the detection of circulating tumour cells", British Medical Bulletin, 2010, vol. 94, No. 1, pp. 49-64.
RosetteSep Human CD45 Depletion Cocktail, [online], VERITAS Corporation, 2005, RosetteSep Procedure and Product Information Sheet, [retrieved from Internet on Nov. 20, 2014 @ <URL:http://www.veritastk.co.jp/attached/1696/15122_15162-PIS.pdf>.
International Search Report for the Application No. PCT/JP2014/076004 dated Dec. 2, 2014.
Written Opinion of the International Searching Authority (PCT/ISA/237) for Application No. PCT/JP2014/076004 dated Dec. 2, 2014.
Supplementary European Search Report for the Application No. EP 14 84 8880 dated Apr. 3, 2017.
Hadi, Esmaeilsabzali et al., "Detection and isolation of circulating tumor cells: Principles and methods", Biotechnology Advances, 2013, vol. 31, No. 7, pp. 1063-1084.
European Office Action for the Application No. 14 848 880.2 dated Jun. 18, 2018.
Notification of Reasons for Refusal for the Application No. 2017-111430 from Japan Patent Office dated Jun. 26, 2018.
European Office Action for the Application No. EP 14 848 880.2 dated Aug. 3, 2020.
European Office Action for the Application No. EP 14 848 880.2 dated Feb. 3, 2021.
The First Office Action for the Application No. 201811278048.3 from The State Intellectual Property Office of the People's Republic of China dated Jun. 30, 2021.

\* cited by examiner

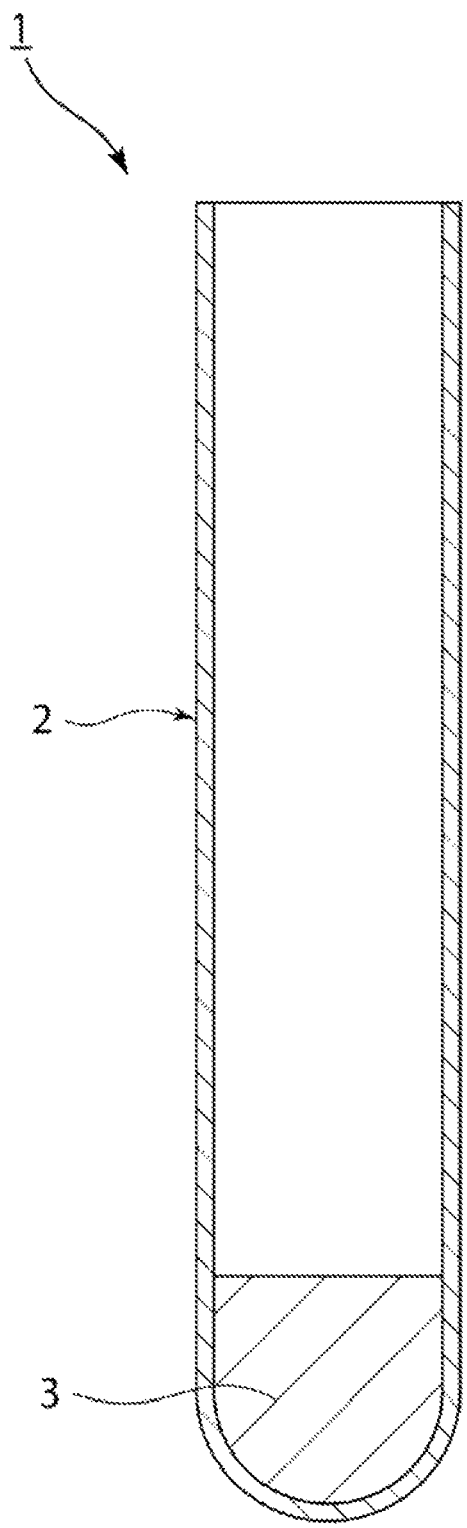

DEVICE FOR CONCENTRATION AND SEPARATION OF CIRCULATING TUMOR CELLS, AND METHOD FOR CONCENTRATION AND SEPARATION OF CIRCULATING TUMOR CELLS

TECHNICAL FIELD

The present invention relates to a device for concentration and separation of circulating tumor cells from a blood-derived specimen. More specifically, the present invention relates to a device for concentration and separation of circulating tumor cells, in which a partition of a cell separating agent can be formed medially between tumor cells and other blood cells after centrifugation using a difference in specific gravity, and a separation method.

BACKGROUND ART

Circulating tumor cells (CTCs) are cancer cells distributed in the peripheral blood by being released from primary tumor tissue or metastatic tumor tissue and infiltrating into the blood. Such circulating tumor cells are greatly associated with cancer metastasis. Thus, attention has been focusing, for example, on the detection of circulating tumor cells and the observation of their dynamics.

Meanwhile, circulating tumor cells are considered to be present only in a trace amount in the blood. Thus, to detect circulating tumor cells or observe the dynamics of circulating tumor cells, it has been necessary to concentrate and separate circulating tumor cells present in the blood to an observable concentration. Various methods have conventionally been proposed as methods for concentration and separation of circulating tumor cells in a blood specimen. For example, a method is known which involves adding a hemolyzing agent to a whole blood specimen to remove erythrocytes as blood cells. However, there has been a problem that many erythrocytes remain unhemolyzed. There has also been a problem that leucocytes cannot be removed. In addition, there has been a problem that the addition of a large amount of the hemolyzing agent to a blood-derived specimen is greatly invasive to intended tumor cells.

The following Patent Literature 1 discloses a method which involves reacting magnetic beads with epithelial cell adhesion molecules (EpCAM) expressed on circulating tumor cells, magnetically sorting tumor cells from other cells, and selectively recovering the tumor cells. The following Patent Literature 2 discloses a method which involves using a hematocyte separation filter to sort tumor cells based on the size of cells. The following Non Patent Literature 1 describes a density-gradient centrifugation method using a commercial separating agent whose specific gravity is considered to be 1.077 g/mL.

CITATION LIST

Patent Literature

Patent Literature 1: Japanese Patent Laid-Open No. 2012-022002
Patent Literature 2: Japanese Patent Laid-Open No. 2013-042689

Non Patent Literature

Non Patent Literature 1: GE Healthcare Bio-Sciences AB "Instructions 71-7167-00 AG Ficoll-Paque PLUS"

SUMMARY OF INVENTION

Technical Problem

The method described in Patent Literature 1 could detect only tumor cells derived from epithelial cells. Consequently, the method has a problem of having a low recovery rate of tumor cells. It also requires a magnetically-labeled antibody, a magnet, and the like and has a complicated operating procedure. In addition, the method requires a lot of time for testing.

The method described in Patent Literature 2 also had a low recovery rate of tumor cells because tumor cells incapable of being recovered by a blood separation filter were present. In addition, it may be incapable of exact concentration and separation.

The method described in Non Patent Literature 1 had sometimes resulted in a local decrease in specific gravity when leucocytes spread below the surface of the separating agent. Consequently, a blood specimen had to be placed so that the interface between the specimen and the separating agent was not disturbed. Thus, its operation was complicated. The method also requires a cautious operation for the recovery of tumor cells. In addition, the interface between the tumor cell layer and the separation medium was unclear. Consequently, the recovery rate of tumor cells was low.

An object of the present invention is to provide a device for concentration and separation of circulating tumor cells and a method for concentration and separation of circulating tumor cells, eliminating the aforementioned drawbacks of the related art and capable of concentrating and separating circulating tumor cells in a blood-derived specimen at a high recovery rate by a simple operation without increasing invasion of cells.

Solution to Problem

In view of the above-described problems, the present inventors have found that a cell separating agent with thixotropic property, having a particular specific gravity can be used to solve the above problems. Specifically, the device according to the present invention is a device for concentration and separation of circulating tumor cells present in a blood-derived specimen, comprising a bottomed tube-shaped container closed at one end and opened at the other end and a cell separating agent with thixotropic property housed in the tube-shaped container and capable of separating tumor cells and blood cells other than the tumor cells after centrifugation, wherein the cell separating agent has a specific gravity ranging from 1.050 to 1.080.

In one particular aspect of the device according to the present invention, the cell separating agent has a specific gravity ranging from 1.055 to 1.080.

In another particular aspect of the device according to the present invention, the cell separating agent has a specific gravity ranging from 1.065 to 1.077.

In another particular aspect of the device according to the present invention, the cell separating agent contains a polyalkylene glycol with a number average molecular weight of 700 or more as an agent imparting a thixotropic property and the polyalkylene glycol is blended at a concentration of 5% by weight or less based on the whole cell separating agent.

In one particular aspect of the device according to the present invention, the device further comprises an anti-blood coagulant housed in the tube-shaped container.

In another particular aspect of the device according to the present invention, the device for concentration and separation of circulating tumor cells further comprises a cell aggregating agent for further selectively aggregating blood cells other than the tumor cells and precipitating the resultant by a centrifugal operation.

In another particular aspect of the device according to the present invention, the cell aggregating agent is an agent for selectively aggregating blood cells.

In another particular aspect of the device according to the present invention, the cell aggregating agent is an antibody having the ability to form an immune complex.

In another particular aspect of the device according to the present invention, the antibody as a cell aggregating agent comprises both of an antigen recognition site capable of binding to an antigen characteristic of the leucocyte surface and an antigen recognition site capable of binding to an antigen characteristic of the erythrocyte surface.

In another particular aspect of the device according to the present invention, the cell aggregating agent is added so that the amount added is 25 to 150 μL based on 1 mL of a blood-derived specimen.

In another particular aspect of the device according to the present invention, the opening of the bottomed tube-shaped container is at least partially sealed by a plug configured to be pierceable and the inside thereof is depressurized.

The method for concentration and separation of circulating tumor cells according to the present invention, comprises the following steps.

(1) A step of allowing a blood-derived specimen, a cell aggregating agent for selectively aggregating blood cells other than tumor cells and precipitating the resultant by a centrifugal operation, and an anti-blood coagulant to coexist in a bottomed tube-shaped container closed at one end and opened at the other end, in which is housed a cell separating agent with a specific gravity ranging from 1.050 to 1.080 enabling the separation of the tumor cells and blood cells other than the tumor cells by a centrifugal operation.

(2) A step of reacting the cell aggregating agent with the blood-derived specimen in the container.

(3) A step of centrifuging the container to form a partition of the cell separating agent between the tumor cells and other blood cells.

(4) A step of recovering the tumor cells concentrated and separated in plasma above the partition.

Advantageous Effects of Invention

According to the device for concentration and separation of circulating tumor cells and the method for concentration and separation in accordance with the present invention, circulating tumor cells in a blood-derived specimen can be concentrated and separated at a high recovery rate by a simple operation without increasing invasion of cells. Hence, circulating tumor cells can be efficiently recovered from a blood-derived specimen.

The device for concentration and separation of circulating tumor cells according to the present invention can recover tumor cells present only in a trace amount in a blood-derived specimen as described above with high purity, and thus, for example, enables an improvement in detection rate and detection accuracy in detecting tumor cells on a flow cytometer using a concentrated and separated specimen. Alternatively, an operation of cytologically analyzing concentrated and separated tumor cells under a microscope can be performed efficiently and with high accuracy. In addition, the ability to recover tumor cells by a simple operation, at a high recovery rate, and with high purity can contribute to the development of a new effective therapeutic agent for tumor and the discovery of a new therapeutic and diagnostic target.

BRIEF DESCRIPTION OF DRAWINGS

FIG. 1 is a schematic sectional front view showing one structural example of the device for concentration and separation of circulating tumor cells according to the present invention.

DESCRIPTION OF EMBODIMENTS

The present invention will be clarified below by describing specific embodiments according to the present invention. The device provided by the present invention is a device for concentrating and separating a trace amount of tumor cells present in a blood-derived specimen, in which a cell separating agent with thixotropic property having a specific gravity intermediate between the tumor cells and other blood cells and enabling the separation of both cells by a centrifugal operation is housed in a bottomed tube-shaped container closed at one end and opened at the other end.

(Blood Cells)

The device for concentration and separation of circulating tumor cells according to the present invention can remove blood cells contained in a blood-derived specimen using a cell aggregating agent to be described later. As used herein, the blood cells represent blood cells present in a blood-derived specimen, other than desired tumor cells, and examples thereof include, but not limited to, hematocyte cells and platelet cells, more specifically, erythrocytes, B cells, T cells, monocytes, NK cells, and granulocytes.

(Specific Gravity of Circulating Tumor Cells and Specific Gravity of Other Blood Cells)

Depending on the type of tumor cells, the specific gravity of circulating tumor cells is generally on the order of 1.040 to 1.065. On the other hand, the specific gravity of erythrocytes is 1.095, and the specific gravity of leucocytes is on the order of 1.063 to 1.085. Thus, the specific gravity of cells other than circulating tumor cells is typically in the range of 1.063 to 1.095.

(Blood-Derived Specimen)

In addition to a specimen as which a whole blood sample collected from a subject is used as it is, the blood-derived specimen herein also includes, for example, one to which any of various agents is added for the retainment of the properties of the blood or for the purpose of adjusting conditions so that they favor the separation and concentration of tumor cells, or the like.

Examples of the agent added to the blood-derived specimen include, but not limited to, saccharides, such as glucose and maltose, and sodium citrate. The anti-blood coagulant to be described later may be configured to be contained in the blood-derived specimen in advance.

(Cell Separating Agent)

The present invention solves the above problems by providing a device in which a cell separating agent with thixotropic property is housed in a bottomed tube-shaped container closed at one end and opened at the other end.

As described above, according to the present invention, it is necessary for the specific gravity of the cell separating agent to be a value between the specific gravity of circulating tumor cells and the specific gravity of blood cells other than the circulating tumor cells. It enables the secure formation of a partition between circulating tumor cells and other blood cells after a centrifugal operation.

Meanwhile, for a cell separating agent with thixotropic property, the flow responsiveness to centrifugal force is generally deteriorated as its specific gravity is increased, and thus the separating agent for serum or plasma commonly used is adjusted to a specific gravity of 1.040 to 1.055.

The specific gravity of the cell separating agent according to the present invention is in the range of 1.050 to 1.080. Thus, tumor cells and other blood cells can be separated. Preferably, the specific gravity is in the range of 1.055 to 1.080, more preferably in the range of 1.065 to 1.077. Still more preferably, the specific gravity is in the range of 1.070 to 1.077. Such a range of specific gravity enables the more secure separation of circulating tumor cells and other blood cells.

However, a higher specific gravity may reduce the fluidity of the cell separating agent. Thus, it is preferable to add a thixotropy enhancer to be described later. As will hereinafter be described, the thixotropy enhancer to be used may be preferably a polyalkylene glycol having a number average molecular weight of 700 or more. Such a thixotropy enhancer can be added to enable the more secure formation of a sufficiently strong partition between tumor cells and other blood cells after centrifugation.

The cell separating agent of the present invention is not particularly limited; however, it preferably contains a liquid component and an inorganic powder. The liquid component and the inorganic powder can be combined to easily provide the above-described range of specific gravity. The inorganic powder may be an inorganic powder whose surface is hydrophilic, or an inorganic powder whose surface is hydrophobic. The inorganic powder may be a combination of an inorganic powder whose surface is hydrophilic and an inorganic powder whose surface is hydrophobic.

In the cell separating agent according to the present invention, the liquid component is not particularly limited, and may be a heretofore known one which is liquid at ordinary temperature, like a silicone-based, α-olefin-fumarate diester copolymer-based, acryl-based, polyester-based, sebacate/2,2-dimethyl-1,3-propanediol/1,2-propanediol copolymer-based, polyether polyurethane-based, polyether ester-based, or other liquid resin, and a liquid/liquid or solid/liquid mixture, such as a liquid mixture of poly-α-pinene polymer and chlorinated hydrocarbon, a liquid mixture of chlorinated polybutene and a liquid compound (e.g., epoxidized an animal or vegetable oil), a liquid mixture of ethylene chloride trifluoride, a benzene polycarboxylic acid alkyl ester derivative, or the like and a polyoxyalkylene glycol or the like, or a liquid mixture of cyclopentadiene oligomer and a phthalate ester or the like.

The inorganic powder is also not particularly limited and may be one or two or more (mixture) selected from the group consisting of silicon dioxide-based fine powders, such as silica produced by a known gas phase process (also referred to as a dry method) and a clay mineral composed of bentonite, smectite, or the like, and titanium oxide-based, alumina-based, or other fine powders.

According to the present invention, the inorganic powder may be hydrophilic or hydrophobic in the surface. The inorganic powder hydrophobic in the surface and the inorganic powder hydrophilic in the surface may be used in combination.

According to the present invention, as the inorganic powder, a silicon dioxide-based powder or a titanium oxide-based powder is preferably used, and both of the powders may be used in combination.

As a hydrophilic silica among silicon dioxide-based powders, for example, a gas-phase process hydrophilic silica, such as Aerosil series, e.g., Aerosil® 90G, 130, 200, or 300, (from Nippon Aerosil Co., Ltd.), Reolosil series, e.g., Reolosil® QS-10, QS-20, or QS-30, (from Tokuyama Corporation), or Wacker HDK series, e.g., Wacker HDK S13, N20, or T30, (from Wacker Asahikasei Silicone Co., Ltd.) is available and easy to use.

As a hydrophobic silica, for example a gas-phase process hydrophobic silica, such as Aerosil series, e.g., Aerosil R972, R974, R805, or R812, (from Nippon Aerosil Co., Ltd.), Reolosil series, e.g., Reolosil MT-10, DM-30S, HM-30S, KS-20S, or PM-20, (from Tokuyama Corporation), or Wacker HDK series, e.g., Wacker HDK H15, H18, or H30, (from Wacker Asahikasei Silicone Co., Ltd.) is easily available and easy to use.

According to the present invention, it is preferable to further add a thixotropy enhancer. The thixotropy enhancer is not particularly limited provided that it enhances thixotropic property; however, a polyalkylene glycol is preferably used. A polymer prepared by polymerizing one or two or more of alkylene oxide monomers having 2 to 4 carbon atoms is more preferably used. A polyalkylene glycol with a number average molecular weight of 700 or more as a polymer prepared by polymerizing one or two or more of alkylene oxide monomers having 3 or 4 carbon atoms is still more preferably used. The addition of such a thixotropy enhancer enables the more secure formation of a partition after centrifugation and enables the formation of a sufficiently strong partition.

In the cell separating agent according to the present invention, the above particular polyalkylene glycols may be used alone, or two or more thereof may be blended.

The polyalkylene glycol used in the present invention excessively containing the polymerization component of ethylene glycol monomer, having 2 carbon atoms, in the molecule is not preferred because of having increased water solubility; one having an HLB value according to Davies' method of 16 or less is preferably used. The HLB value according to Davies' method is calculated by the following equation.

<HLB value=7+the sum of the hydrophilic group numbers−the sum of the lipophilic group numbers>

The group number refers to a specific numerical value assigned to each functional group.

Depending on the hydroxyl group number derived from the functional group number of an alcohol providing a starting substance, or depending on the presence of the capping of the hydroxyl group with an alkyl group or the like, polyalkylene glycols having one or more than one hydroxyl group are each used. To reduce water solubility, the hydroxyl group number per molecule is preferably 3 or less.

A hydrophobic residue introduced except for the purpose of capping the hydroxyl group may be contained in the molecule of the polyalkylene glycol. Examples of the hydrophobic residue include an alkylene group, an alkene group, an alkyne group, an aromatic ring group, and a dimethylsiloxane-based substituent group.

The molecule may contain, in place of the hydroxyl group or additionally, a hydrogen-bonding polar group, such as a carbonyl group, an amino group, or a thiol group. To reduce water solubility, the polar group number per molecule is again preferably 3 or less.

A number average molecular weight of the polyalkylene glycol of less than 700 sometimes results in the generation of cracks in the partition formed after centrifugation. Consequently, hematocyte cells can mix with tumor cells to reduce the purity of the tumor cells. Thus, it is preferable for the number average molecular weight to be 700 or more. More preferably, the number average molecular weight is preferably 1,000 or more for the polyalkylene glycol having two or more hydroxyl groups. The upper limit value of the number average molecular weight of the polyalkylene glycol is not particularly limited; however, it is preferably 100,000 or less. Above 100,000, it has a reduced hydroxyl group density and may not act as a thixotropy enhancer.

The concentration of the polyalkylene glycol is preferably 5% by weight or less based on the whole blood separating agent. The concentration of 5% by weight or less can more easily adjust the cell separating agent to a desirable viscosity range. It is more preferably 3% by weight or less, still more preferably 2% by weight or less. The lower limit of the concentration of the polyalkylene glycol is preferably 0.1% by weight. The concentration of 0.1% by weight or more can easily adjust the viscosity range of the cell separating agent to a desirable range.

Specific examples of the particular polyalkylene glycol can include the following various polyalkylene glycols. However, they are not intended to be limited to the substances exemplified below.

Examples of the polyalkylene glycol having more than one terminal hydroxyl group include polybutylene glycols (Uniol® PB series, such as PB-700, PB-1000, and PB-2000, from NOF Corporation), polypropylene glycols (Uniol D series, such as D-700, D-1200, and D-4000, from NOF Corporation), polyoxypropylene glyceryl ethers (Uniol TG series, such as TG-1000, TG-3000, and TG-4000, from NOF Corporation), polyoxypropylene sorbitols (Uniol HS series, such as HS-1600D, from NOF Corporation), polyserines (Polyserine DCB series, such as DCB-1000, DCB-2000, and DCB-4000, and Polyserine DC series, such as DC-1100, DC-1800E, and DC-3000E, from NOF Corporation), polyoxypropylene diglyceryl ethers (Unilube® series, such as DGP-700, from NOF Corporation), polyoxypropylene glyceryl ethers (Preminol series, such as S3003, S3006, and S3011, from Asahi Glass Co., Ltd.), polypropylene glycols (Preminol® series, such as S4001, S4006, S4011, and S4015, from Asahi Glass Co., Ltd.), polyoxyethylene polyoxypropylene glycols (New Pole® PE series, such as PE-34, PE 61, PE-62, PE-64, PE-71, and PE-74, from Sanyo Chemical Industries, Ltd.), and polyoxyethylene polyoxypropylene glyceryl ethers (Adeka Polyether, such as AM-502, from Adeka Corporation).

Examples of the polyalkylene glycol having one terminal hydroxyl group include polyoxypropylene butyl ethers (Unilube MB series, such as MB-7, MB-14, MB-38, and MB-700, from NOF Corporation), polyoxypropylene glycol monoethers (New Pole LB series, such as LB-285, LB-625, LB-3000, and LB-1800X, from Sanyo Chemical Industries, Ltd.) and polyoxypropylene alkyl ethers (Preminol series, such as S1004F and S1005, from Asahi Glass Co., Ltd.).

In the cell separating agent according to the present invention, additives, such as a compatibilizer and an antioxidant, may be further blended in the range allowing the maintenance of performance as a cell separating agent.

The specific gravity of the cell separating agent according to the present invention is adjusted to 1.050 to 1.080. The specific gravity of the cell separating agent according to the present invention is preferably adjusted to 1.055 to 1.080, more preferably 1.065 to 1.077. A specific gravity of less than 1.055 sometimes decreases the recovery rate of desired tumor cells probably because the specific gravity is lower than that of the tumor cells. On the other hand, a specific gravity of more than 1.080 sometimes reduces the fluidity of the cell separating agent in centrifugation to make it impossible to form a partition medially between tumor cells and other blood cells because it becomes close to the specific gravity of undesired blood cells other than tumor cells, particularly hematocyte cells.

(Anti-Blood Coagulant)

An anti-blood coagulant may be added to the device for concentration and separation of tumor cells according to the present invention, if necessary. The anti-blood coagulant may be in a form coexisting with a cell aggregating agent to be described later and a blood-derived specimen when the agent is reacted with the specimen. Specifically, the anti-blood coagulant may be in a form housed in the container in advance, or may be in a form separately added to the blood-derived specimen in advance. When the anti-blood coagulant is in a form housed in the container in advance, it may be in a form applied to the inner wall surface of the container or in a form housed in the container by being made in a shape easily dissolvable in the blood-derived specimen, such as in a granular shape or a sheet shape.

The anti-blood coagulant used in the present invention is not particularly limited; known anti-blood coagulants, such as citric acid, heparin, and EDTA, can be used.

(Cell Aggregating Agent)

The device for concentration and separation of tumor cells according to the present invention contains a cell aggregating agent, if necessary. The cell aggregating agent according to the present invention means an agent capable of selectively aggregating blood cells other than desired tumor cells to facilitate the precipitation and separation thereof by a centrifugal operation using a difference in specific gravity to increase the purity of the tumor cells. For that reason, any known agent can be applied provided that it is an agent having such an action mechanism; however, an antibody having both of an antigen recognition site capable of binding to an antigen characteristic of the leucocyte surface and an antigen recognition site capable of binding to an antigen characteristic of the erythrocyte surface (RosetteSep human CD45 depletion cocktail, from STEMCELL Technologies, Inc.) is preferably used.

As an agent having a different mechanism of aggregation, an agent in which an antigen recognition site capable of binding to an antigen characteristic of the leucocyte surface is physically or chemically bound to a carrier having a high specific gravity, or an agent for physically adsorbing hematocyte cells to an insoluble carrier, such as microbeads can also be used.

(Method for Producing Cell Separating Agent)

The method for producing a cell separating agent according to the present invention may be a heretofore known method and is not particularly limited. Specifically, the above-described liquid component, the above-described inorganic powder, and the above-described particular polyalkylene glycol may be mixed by a proper method. The mixing method is not particularly limited; examples thereof can include methods using known kneading machines, such as a planetary mixer, a roll mill, and a homogenizer.

(Device for Concentration and Separation of Circulating Tumor Cells)

The device for concentration and separation of circulating tumor cells according to the present invention comprises, as constituents, a container body, and the cell separating agent and, if necessary, the anti-blood coagulant and the cell aggregating agent according to the present invention which are housed in the container body. The container body is not particularly limited, and may be any bottomed tube-shaped container capable of being centrifuged, such as a test tube, a centrifuge tube, or a microtube, including a bottomed tube-shaped container widely used as a blood-collecting vessel.

FIG. 1 is a schematic sectional front view showing one structural example of such a device for concentration and separation of circulating tumor cells. Device for concentration and separation of circulating tumor cell 1 comprises container body 2 consisting of a bottomed tube-shaped container. Cell separating agent 3 is housed in the container body 2.

One opened end of the bottomed tube-shaped container is at least partially sealed by a plug configured to be pierceable, and the inside of the container may be depressurized. The material of the container body is also not particularly limited provided that it can withstand centrifugation; any material, such as synthetic resin or glass, can be used.

The container body and the plug may each be subjected to inner surface treatment in order to achieve the effect of preventing blood clot adhesion or the like.

The addition amount of the cell separating agent is typically preferably on the order of 0.3 g to 3.0 g per container; however, the optimum addition amount can be selected depending on the volume and shape of the container used.

In the device for concentration and separation of circulating tumor cells according to the present invention, the cell aggregating agent is preferably housed in the container so that its addition amount is 25 to 150 μL based on 1 mL of the blood-derived specimen. It enables the more effective separation of tumor cells and blood cells other than tumor cells in accordance with the present invention.

Also included in the present invention is the use of a device for concentration and separation of circulating tumor cells in a blood-derived specimen. The present invention provides the use of a device for concentration and separation of circulating tumor cells present in a blood-derived specimen, comprising a bottomed tube-shaped container closed at one end and opened at the other end and a cell separating agent with thixotropic property housed in the tube-shaped container and capable of separating tumor cells and blood cells other than the tumor cells after centrifugation, the cell separating agent having a specific gravity ranging from 1.050 to 1.080.

As described above, the use of the device for concentration and separation of circulating tumor cells according to the present invention can provide a method for concentrating and separating tumor cells in a blood-derived specimen. The method for concentrating and separating tumor cells in a blood-derived specimen using the device for concentration and separation of circulating tumor cells according to the present invention comprises the following steps.

(Method for Concentrating and Separating Circulating Tumor Cells in Blood-Derived Specimen Using Device for Concentration and Separation of Circulating Tumor Cells)

(1) A step of allowing a blood-derived specimen, a cell aggregating agent for selectively aggregating blood cells other than tumor cells and precipitating the resultant by a centrifugal operation, and an anti-blood coagulant to coexist in a bottomed tube-shaped container closed at one end and opened at the other end, in which is housed a cell separating agent with a specific gravity ranging from 1.050 to 1.080 enabling the separation of the tumor cells and blood cells other than the tumor cells by a centrifugal operation, (2) A step of reacting the cell aggregating agent with the blood-derived specimen in the container, (3) A step of centrifuging the container to form a partition of the cell separating agent between the tumor cells and other blood cells, and (4) A step of recovering the tumor cells concentrated and separated in the plasma above the partition.

Details regarding the device are as described above, and a person skilled in the art reading the present specification can carry out the method for concentrating and separating circulating tumor cells in a blood-derived specimen according to the present invention by referring to the description of the specification and properly making modifications or the like.

The circulating tumor cells concentrated and separated using the device according to the present invention can be counted and analyzed using a method, such as flow cytometry, after labeling with a detection reagent. Examples of the detection reagent include a reagent containing an antibody recognizing a characteristic antigen expressed on the surface of circulating tumor cells, and a reagent containing a virus capable of infecting tumor cells, proliferating in response to telomerase activity characteristic of tumor cells, and emitting fluorescence.

The use of the device of the present invention enables the recovery of tumor cells with high purity, and thus is expected to improve the efficiency and accuracy of the detection of tumor cells using a flow cytometer.

EXAMPLES

The present invention will be clarified below by giving specific Examples and Comparative Examples of the present invention. However, the present invention is not intended to be limited to the following Examples.

Examples 1 to 12 and Comparative Examples 1 to 2

Substances Used in Examples 1 to 12 and Comparative Examples 1 to 2

1) Liquid Component

Liquid component 1: acrylic ester polymer (specific gravity: 1.032, viscosity at 25° C.: 65 Pa. s)

Viscosity was measured using a rheometer, DV-III (Brookfield AMETEK, Inc.).

2) Inorganic Powder

As an inorganic powder, a combination of hydrophobic silica (Aerosil R974 from Nippon Aerosil Co., Ltd., particle diameter: about 12 nm, specific surface area: about 170 $m^2/g$, made hydrophobic by chemically treating the surface with a CH: group) and titanium oxide (Tipaque A-100 from Ishihara Sangyo Kaisha, Ltd., particle diameter: 0.15 μm) was used.

3) Polyalkylene Glycol

Polyalkylene glycols as shown in Table 1 below were used as thixotropy enhancers 1 to 3.

Enhancer 1: polyoxypropylene glyceryl ether (Preminol S3011 from Asahi Glass Co., Ltd.)

Enhancer 2: polybutylene glycol (Uniol PB700 from NOF Corporation)

Enhancer 3: polyoxypropylene glyceryl ether (Adeka Polyether G300 from Adeka Corporation)

TABLE 1

|  | Substance Name | Trade Name | Mn | HLB (Davies' Method) |
|---|---|---|---|---|
| Enhancer 1 | Polyoxypropylene Glyceryl Ether | S3011 | 10,000 | −13 |
| Enhancer 2 | Polybutylene Glycol | PB700 | 700 | 5 |
| Enhancer 3 | Polyoxypropylene Glyceryl Ether | G300 | 350 | 12 |

Preparation of Cell Separating Agent

Example 1

As shown in Table 2 below, liquid component 1, the inorganic powder as a mixture, and thixotropy enhancer 1 shown in Table 1 as a polyalkylene glycol were blended in amounts of 94.9% by weight, 4.6% by weight, and 0.5% by weight, respectively and stirred and mixed using a planetary mixer at room temperature to prepare a cell separating agent.

Examples 2 to 12 and Comparative Examples 1 to 2

Cell separating agents were prepared in the same way as in Example 1 except for changing the material and blending ratio used as shown in Table 2 below. In Example 11, no polyalkylene glycol was used. In Example 12, thixotropy enhancer 3, having a number average molecular weight of 350, was used. In Comparative Example 1, the cell separating agent was adjusted to a specific gravity of 1.045. In Comparative Example 2, the cell separating agent was adjusted to a specific gravity of 1.085.

TABLE 2

| | Liquid Component | Inorganic Powder (% by weight) | | Polyalkylene Glycol | | Specific Gravity of Cell separating |
|---|---|---|---|---|---|---|
| | % by weight | R974 | A-100 | Type | % by weight | agent |
| Example 1 | 94.9 | 4.0 | 0.6 | Enhancer 1 | 0.5 | 1.055 |
| Example 2 | 93.7 | 4.0 | 1.8 | Enhancer 1 | 0.5 | 1.065 |
| Example 3 | 93.0 | 4.0 | 2.5 | Enhancer 1 | 0.5 | 1.071 |
| Example 4 | 91.0 | 4.0 | 2.5 | Enhancer 1 | 2.5 | 1.071 |
| Example 5 | 88.5 | 4.0 | 2.5 | Enhancer 1 | 5.0 | 1.071 |
| Example 6 | 93.0 | 4.0 | 2.5 | Enhancer 2 | 0.5 | 1.071 |
| Example 7 | 88.5 | 4.0 | 2.5 | Enhancer 2 | 5.0 | 1.071 |
| Example 8 | 92.5 | 4.0 | 3.0 | Enhancer 1 | 0.5 | 1.077 |
| Example 9 | 92.0 | 4.0 | 3.5 | Enhancer 1 | 0.5 | 1.080 |
| Example 10 | 83.5 | 4.0 | 2.5 | Enhancer 1 | 10.0 | 1.071 |
| Example 11 | 93.5 | 4.0 | 2.5 | — | — | 1.071 |
| Example 12 | 93.0 | 4.0 | 2.5 | Enhancer 3 | 0.5 | 1.071 |
| Comp. Ex. 1 | 96.5 | 3.0 | 0.0 | Enhancer 1 | 0.5 | 1.045 |
| Comp. Ex. 2 | 91.5 | 4.0 | 4.0 | Enhancer 1 | 0.5 | 1.085 |

(Preparation of Device for Concentration and Separation of Circulating Tumor Cells)

15-mL Conical tubes (from BD Biosciences) were used, and about 1.8 g each of the cell separating agents of Examples 1 to 12 and Comparative Examples 1 to 2 were housed in the tubes to prepare devices for concentration and separation of circulating tumor cells.

(Evaluation)

The following evaluation was carried out using a patient pseudo-blood in which colon adenocarcinoma cultured cells (DLD-1) were added to 50 cells/mL of blood to human normal blood subjected to anticoagulation treatment with EDTA.

1) Fluidity Evaluation of Cell Separating Agent

After pouring 2 mL of a patient pseudo-blood into each of 3 devices for concentration and separation of circulating tumor cells, centrifugation was carried out under conditions of 1,200 g×20 minutes/room temperature. The case where the partition of the cell separating agent had an average thickness of 5 mm or more was denoted by "good"; the case where it had a thickness of 2 mm (inclusive) to 5 mm (exclusive) was denoted by "fair"; and the case where it had a thickness of less than 2 mm was determined as "poor". The results are shown in Table 3 below.

2) Partition Strength

Each device for concentration and separation of circulating tumor cells after centrifugation was caused to fall sideways and given vibration at 60 Hz for 1 hour. The case where the partition was not moved was determined as "good"; the case where it was moved but was kept intact, "fair"; and the case where the partition was disrupted and mixed with hematocyte cells, "poor". The results are shown in Table 3 below.

3) Evaluation of State of Partition Formation

The state of the partition formed after centrifugation and the presence of oily suspended matter and oil film were visually observed. The results are shown in Table 3 below. In Table 3, the case where cracks occurred on the partition was described as "cracking". The case where oily suspended matter and oil film formed was described as "fair/oil". The case where none of these were observed was described as "good".

4) Tumor Cell Recovery Rate

After centrifugation, the tumor cells concentrated and separated in plasma above the partition were suspended and recovered by pipetting. Since DLD-1 was epithelial cells, CD326-FITC antibody (from Miltenyi Biotec) was added to the recovered suspension to perform fluorescent labeling. Remaining undesired leucocytes were fluorescently labeled with CD45-APC (from Miltenyi Inc.); the number of CD326+/CD45− cells was counted using a flow cytometer (FACSAria from BD Co., Ltd.); and the recovery rate based on the number (100 cells) of tumor cells contained in the patient pseudo-blood was calculated. The results are shown in Table 3.

TABLE 3

|  | Fluidity (1200 G × 20 min./ Room Temp.) | Partition Strength | State of Partition Formation | Tumor Cell Recovery Rate (%) |
|---|---|---|---|---|
| Example 1 | Good | Good | Good | 65 |
| Example 2 | Good | Good | Good | 80 |
| Example 3 | Good | Good | Good | 95 |
| Example 4 | Good | Good | Good | 90 |
| Example 5 | Good | Good | Good | 91 |
| Example 6 | Good | Good | Good | 89 |
| Example 7 | Good | Good | Good | 91 |
| Example 8 | Good | Good | Good | 95 |
| Example 9 | Good | Good | Good | 92 |
| Example 10 | Good | Fair | Fair/Oil | 89 |
| Example 11 | Good | Fair | Cracking | 85 |
| Example 12 | Good | Good | Cracking | 86 |
| Comp. Ex. 1 | Good | Good | Good | 39 |
| Comp. Ex. 2 | Poor | — | — | — |

As shown in Table 3, in Examples 1 to 9, favorable results were shown for all of the cell separating agent fluidity, the partition strength, the partition formation state, and the tumor cell recovery rate. In Example 10, oily suspended matter and oil film formed in the observation of the partition formation state and the partition strength was slightly low, but tumor cells could be recovered at a high recovery rate as in Examples 1 to 9. In Example 10, the addition of the polyoxyalkylene glycol in an amount of as much as 10% by weight probably produced the oily suspended matter and oil film.

In contrast, in Example 11 where no polyalkylene glycol was added, sufficient thixotropic property was not obtained and sufficient partition strength was also not obtained, but the recovery rate of tumor cells was favorable.

In Example 12 where the polyalkylene glycol having an average molecular weight of 350 was used, cracks formed on the partition after centrifugation although the recovery rate of tumor cells was favorable. Even the use of the polyalkylene glycol having an average molecular weight of 350 probably did not result in the formation of a sufficiently strong partition because it did not sufficiently increase the thixotropic property, as in Example 11. However, in Example 12, although a sufficiently strong partition was probably not formed, the recovery rate of tumor cells was also favorable as in Example 11.

When a sufficient partition strength is not obtained or cracks form on the partition, the leakage of hematocytes and tumor cells separated by the separating agent can occur. This may affect the recovery rate of tumor cells and may result in the mixing of hematocytes in the liquid phase containing the recovered tumor cells.

In Comparative Example 1 where the specific gravity of the cell separating agent was adjusted to 1.045, the fluidity, the partition strength, and the partition state were favorable but the recovery rate of tumor cells was as low as 39%. In Comparative Example 2 where the specific gravity of the cell separating agent was adjusted to 1.085, centrifugation did not result in the formation of a partition.

Hence, the specific gravity of the cell separating agent is preferably adjusted to 1.055 to 1.080. In addition, to enable tumor cells to be obtained at a higher recovery rate and make the fluidity of the cell separating agent higher, the specific gravity of the cell separating agent is preferably adjusted to 1.065 to 1.077.

Examples 13 to 18

The following Examples 13 to 18 where a blood-derived specimen and a cell aggregating agent coexist will be described.

In the following evaluation, the same device for concentration and separation of circulating tumor cells and patient pseudo-blood as those in Example 3 were used.

Example 13

RosetteSep human CD45 depletion cocktail (from STEM-CELL Technologies, Co., Inc.) was used as a cell aggregating agent. 10 μL (5 μL/1 mL of blood) of the cell aggregating agent was added to 2 mL of the patient pseudo-blood subjected to anticoagulation treatment with EDTA, which was then mixed by shaking and allowed to stand at room temperature for 20 minutes, followed by centrifugation under conditions of 1,200 G×20 minutes/room temperature.

After centrifugation, the tumor cells concentrated and separated in plasma above the partition were suspended and recovered by pipetting. The recovered suspension was subjected to fluorescent labeling with CD326-FITC antibody (from Miltenyi Inc.) and CD45-APC (from Miltenyi Inc.), and the number of CD326+/CD45− cells and the total number of cells were counted using a flow cytometer (FACSAria from BD Co., Ltd.) to calculate the recovery rate based on the number (100 cells) of tumor cells contained in the patient pseudo-blood and the number of remaining undesired blood cells other than the tumor cells. The results are shown in Table 4.

Examples 14 to 18

Evaluation was carried out in the same way as in Example 13 except for changing the addition amount of the cell aggregating agent as shown in Table 4 below. The results are shown in Table 4. In the Table, the addition amount of the cell aggregating agent and the number of blood cells other than tumor cells are given in terms of per mL of the blood-derived specimen.

TABLE 4

|  | Addition Amount of Cell aggregating agent (μL/1 mL of Blood) | Tumor Cell Recovery Rate (%) | Number of Nucleated Cells Other Than Tumor Cells (Cells/1 mL of Blood) |
|---|---|---|---|
| Example 3 | 0 | 95 | 2438560 |
| Example 13 | 5 | 88 | 1087873 |
| Example 14 | 10 | 93 | 499884 |
| Example 15 | 25 | 90 | 161254 |
| Example 16 | 50 | 96 | 108933 |
| Example 17 | 100 | 92 | 84453 |
| Example 18 | 150 | 89 | 148634 |

As shown in Table 4, as the addition amount of the cell aggregating agent based on 1 mL of the blood-derived specimen was increased, the number of the blood cells other than tumor cells decreased. The addition of 25 μL or more of the cell aggregating agent based on 1 mL of the blood-derived specimen markedly decreased the number of remaining blood cells other than tumor cells. Thus, the results show that the addition amount of the cell aggregating agent is preferably 25 μL or more based on 1 mL of the blood-derived specimen.

In Examples 13 to 17, as the addition amount of the cell aggregating agent was increased, the number of blood cells other than tumor cells progressively decreased. However, in Example 18, the number of remaining such blood cells tended to slightly increase. Thus, the addition amount of the cell aggregating agent is preferably set to 150 μL or less based on 1 mL of the blood-derived specimen.

Hence, the addition amount of the cell aggregating agent based on 1 mL of the blood-derived specimen is preferably set to 25 µL to 150 µL.

As seen from the results of Table 4, the device for concentration and separation of tumor cells containing a cell separating agent could be used with about 5,300,000,000 blood cells present in 1 mL of the blood-derived specimen to easily remove blood cells other than tumor cells in the blood-derived specimen to about 1/2,000. The addition amount of the cell aggregating agent in the blood-derived specimen could be set to a preferable range of 25 µL to 150 µL to easily remove blood cells other than tumor cells to about 1/50,000 cells. The recovery rate of tumor cells was again high.

It is probable that the recovery of tumor cells present only in a trace amount in a blood-derived specimen with high purity is expected to improve the efficiency and accuracy of the detection of tumor cells using a flow cytometer or enables the operation of cytologically analyzing tumor cells under a microscope to be performed efficiently and with high accuracy. In addition, the device for concentration and separation of tumor cells according to the present invention can recover tumor cells at a high recovery rate and with high purity by a simple operation and thus can probably contribute to developing a new effective therapeutic agent for tumor and help find out a new therapeutic and diagnostic target.

REFERENCE SIGNS LIST

1 Device for Concentration and Separation of Circulating Tumor Cells
2 Container Body
3 Cell separating agent

The invention claimed is:

1. A device for concentration and separation of circulating tumor cells present in a blood-derived specimen, comprising:
   a bottomed tube-shaped container closed at one end and opened at the other end; and
   a cell separating agent with thixotropic property housed in the tube-shaped container and capable of separating tumor cells and blood cells other than the tumor cells after centrifugation,
   wherein the cell separating agent comprises a liquid component and inorganic powders and has a specific gravity ranging from 1.065 to 1.080,
   the inorganic powders comprise silica and a non-silica powder, and
   the cell separating agent comprises a polyalkylene glycol with a number average molecular weight of 700 or more as an agent imparting a thixotropic property and the polyalkylene glycol is blended at a concentration of 5% by weight or less based on the whole cell separating agent.

2. The device for concentration and separation of circulating tumor cells according to claim 1, wherein the cell separating agent has a specific gravity ranging from 1.065 to 1.077.

3. The device for concentration and separation of circulating tumor cells according to claim 1, further comprising an anti-blood coagulant housed in the tube-shaped container.

4. The device for concentration and separation of circulating tumor cells according to claim 1, further comprising a cell aggregating agent for further selectively aggregating blood cells other than the tumor cells and precipitating the resultant by a centrifugal operation.

5. The device for concentration and separation of circulating tumor cells according to claim 4, wherein the cell aggregating agent is an antibody having the ability to form an immune complex.

6. The device for concentration and separation of circulating tumor cells according to claim 5, wherein the antibody as a cell aggregating agent comprises both of an antigen recognition site capable of binding to an antigen characteristic of the leucocyte surface and an antigen recognition site capable of binding to an antigen characteristic of the erythrocyte surface.

7. The device for concentration and separation of circulating tumor cells according to claim 4, wherein the cell aggregating agent is added so that the amount added is 25 to 150 µL based on 1 mL of a blood-derived specimen.

8. The device for concentration and separation of circulating tumor cells according to claim 1, wherein the opening of the bottomed tube-shaped container is at least partially sealed by a plug configured to be pierceable and the inside thereof is depressurized.

9. A method for concentrating and separating circulating tumor cells in a blood-derived specimen, comprising using the device according to claim 1 and employing the following steps:
   (1) a step of allowing a blood-derived specimen, a cell aggregating agent for selectively aggregating blood cells other than tumor cells and precipitating the resultant by a centrifugal operation, and an anti-blood coagulant to coexist in the bottomed tube-shaped container;
   (2) a step of reacting the cell aggregating agent with the blood-derived specimen in the container;
   (3) a step of centrifuging the container to form a partition of the cell separating agent between the tumor cells and other blood cells; and
   (4) a step of recovering the tumor cells concentrated and separated in plasma above the partition.

10. The device for concentration and separation of circulating tumor cells according to claim 2, wherein the opening of the bottomed tube-shaped container is at least partially sealed by a plug configured to be pierceable and the inside thereof is depressurized.

11. The device for concentration and separation of circulating tumor cells according to claim 3, wherein the opening of the bottomed tube-shaped container is at least partially sealed by a plug configured to be pierceable and the inside thereof is depressurized.

12. The device for concentration and separation of circulating tumor cells according to claim 4, wherein the opening of the bottomed tube-shaped container is at least partially sealed by a plug configured to be pierceable and the inside thereof is depressurized.

13. The device for concentration and separation of circulating tumor cells according to claim 1, wherein the non-silica powder is at least one selected from the group consisting of a clay mineral composed of bentonite, a clay mineral composed of smectite, titanium oxide-based powder and alumina-based powder.

14. The device for concentration and separation of circulating tumor cells according to claim 13, wherein the non-silica powder is titanium oxide-based powder.

* * * * *